United States Patent [19]

Dria et al.

[11] 4,455,434
[45] Jun. 19, 1984

[54] PROCESS FOR THE PREPARATION OF MALEIC ANHYDRIDE

[75] Inventors: Dennis E. Dria, Cleveland Heights; Noel J. Bremer, Kent, both of Ohio

[73] Assignee: The Standard Oil Company, Cleveland, Ohio

[21] Appl. No.: 470,681

[22] Filed: Feb. 28, 1983

Related U.S. Application Data

[62] Division of Ser. No. 392,961, Jun. 28, 1982, Pat. No. 4,400,306.

[51] Int. Cl.³ .......................................... C07D 307/60
[52] U.S. Cl. .................................... 549/260; 549/259
[58] Field of Search ................................ 549/259, 260

[56] References Cited

U.S. PATENT DOCUMENTS

| | | | |
|---|---|---|---|
| 3,962,189 | 6/1976 | Russin et al. | 252/428 |
| 4,188,471 | 2/1980 | Nasser, Jr. et al. | 252/431 R |
| 4,224,428 | 9/1980 | Kirch et al. | 252/428 |
| 4,250,286 | 2/1981 | Shipley | 252/429 B |
| 4,256,609 | 3/1981 | Dale et al. | 252/455 Z |

*Primary Examiner*—John M. Ford
*Assistant Examiner*—Bernard Dentz
*Attorney, Agent, or Firm*—Joseph G. Curatolo; Larry W. Evans

[57] ABSTRACT

A process is provided for preparing supported catalysts by impregnating a pre-formed support with a solution of a metal alkoxide and contacting the impregnated support with a solution of at least one additional catalyst component. This process is particularly suitable for forming attrition resistant fluidizable catalysts. Catalysts prepared by this method are useful in various reaction processes, and may be utilized in oxidation processes such as the production of maleic anhydride from 4 carbon atom hydrocarbons.

6 Claims, No Drawings

PROCESS FOR THE PREPARATION OF MALEIC ANHYDRIDE

This is a continuation of application Ser. No. 392,961 filed June 28, 1982 now U.S. Pat. No. 4,400,306.

BACKGROUND OF THE INVENTION

This invention relates to a process for the preparation of supported catalysts, including fluid-bed catalysts by the impregnation of a pre-formed support with at least one metal alkoxide. The present invention also is directed to a process for the preparation of fluid-bed catalysts containing the mixed oxides of vanadium and phosphorus by the impregnation of a pre-formed fluidizable support with a vanadium alkoxide and subsequent reaction with a phosphorus containing compound. The vanadium phosphorus oxide containing fluid-bed catalyst is useful for the production of maleic anhydride from hydrocarbons, such as n-butane, n-butenes, 1,3-butadiene or mixtures thereof.

Fluid-bed catalysts have conventionally been prepared in various ways. In one method of preparation, catalyst component containing compounds and support materials are contacted in a solution or slurry, possibly with heating, and the mixture is thereafter dried. The resulting solid is then ground and screened to a proper fluidizable size, such that the catalyst particles have a particle size of about 20 microns to about 300 microns.

Another method of preparation of fluid-bed catalysts is the oil drop technique, in which a solution or slurry of catalyst components and support materials are dropped into a hot oil bath, to form substantially microspheroidal particles capable of fluidization. Another method of preparation includes the spray drying of a solution or slurry of catalyst components and support material to obtain microspheroidal particles.

Another method for obtaining supported catalysts is by the impregnation of a previously formed and commercially available fluidizable support material with a solution of the catalyst or the catalyst components.

When the catalyst components and support materials are mixed toeghter, it is necessary in order to obtain suitable physical integrity for the fluidizable catalyst, to precisely match physical characteristics and affinities of the catalytic and support components so that these might bind more readily, whether physically or chemically, to withstand the attritting forces of commercial fluid-bed reactors. To attain proper attrition resistance, it is often required that particular proportions of support material versus catalytic material be achieved in the mixture. If the catalyst components are mixed before the fluidizable catalyst particles are formed, then a certain portion of the fluidizable catalyst particles so formed may lack the required proportion of support material. If a lesser amount of support material is incorporated, the attrition resistance will be lessened and the particle will be subject to attrition or fracture during use. If too great a portion of support material is present in the catalyst particle, the catalytic activity of that particle may be diminished.

One method for obtaining attrition resistant particles is to use an attrition resistant fluidizable support material which has been pre-formed. When these supports are impregnated with the catalytic material, however, maximum catalytic efficiency is not readily achieved.

SUMMARY OF THE INVENTION

It is therefore an object of the present invention to provide a process for preparing supported catalysts by impregnating a preformed support with a metal alkoxide.

It is a further object of the present invention to provide a process of preparing fluidizable catalysts which are attrition resistant and highly active catalytically.

It is a further object of the present invention to provide a process for preparing fluid-bed catalysts containing the mixed oxides of vanadium and phosphorus.

It is a further object of the present invention to provide a process for producing maleic anhydride from 4 carbon atom hydrocarbons utilizing fluid-bed vanadium phosphorus mixed oxide catalysts.

We have found that excellent, attrition resistant and highly active fluidizable catalysts can be obtained by introducing the catalytic components into the pores of a pre-formed fluidizable support material. The support material is impregnated with a solution of a metal alkoxide, such that the metal component is deposited within the pores of the support material. The metal containing support may then be contacted with a solution of additional catalyst components, under conditions which permit the additional components to react or interact with the metal deposited within the pores of the support material, thereby forming the catalyst in situ.

In general, the process of the present invention includes the preparation of a supported catalyst comprising impregnating a pre-formed catalyst support with a solution of an alkoxide of at least one metal selected from vanadium, molybdenum, antimony, copper, niobium, tantalum, zinc, zirconium, boron and mixtures thereof, contacting the impregnated support with a solution of at least one additional catalyst component to form the catalyst in situ, and drying the thus formed catalyst-containing support.

In one embodiment of the invention, the pre-formed catalyst support is a fluidizable support. Also in one embodiment of the invention, a pre-formed fluidizable catalyst support material is contacted with a solution of a vanadium alkoxide, and is thereafter contacted with a solution of a phosphorus containing compound prior or subsequent to reducing at least a portion of the vanadium to a valence state of +4. The thus formed vanadium and phosphorus oxide containing fluidizable catalyst is useful in the production of maleic anhydride by the oxidation of 4 carbon atom hydrocarbons such as n-butane, n-butene, 1,3-butadiene and mixtures thereof.

DETAILED DESCRIPTION OF THE INVENTION

The fluidizable support material to be utilized in preparing fluid-bed catalysts according to the process of the present invention should have particle sizes which fall in the range of about 20 microns to about 300 microns, preferably between 20 microns to about 240 microns. These supports should be microporous, and preferably have an intrinsic surface area in the range of about 0.1 m²/g, to about 500 m²/g.

The support materials or carriers used are generally inert to the reaction catalyzed by the supported catalyst. Suitable catalyst support materials including fluidizable support materials which exhibit the required attrition resistance for fluid-bed catalysis operation, include alumina, alumina-silica, Alundum, silica, zirconia, niobia, zirconium phosphate, tin oxide, zinc oxide, silicon carbide, montmorillonite clays, titanium dioxide and the like. An example of commercially available support materials which may be utilized in the process of the present invention include F-7 silica (available from the Norton Company) and Norton fluidizable alumina (also available from the Norton Company).

The metal alkoxides which are suitable for use in impregnating the fluidizable support materials according to the process of the present invention include the alkoxides of V, Mo, Sb, Cu, Nb, Ta, Zn, Zr, B and mixtures thereof. Suitable alcohol adducts or alkoxide moieties include but are not limited to methoxide, ethoxide, propoxide, isopropoxide, t-butoxide, n-butoxide, isobutoxide and the like. Metal alkoxides are available commercially, and can be prepared by a variety of known synthesis.

The support material can be impregnated with the metal alkoxide by slurrying the support in a solution of the metal alkoxide, or by adding the solution in small increments to the support, with agitation. The solvent for the metal alkoxide is preferably organic, and is most preferably the alcohol corresponding to the alkoxide moiety.

We have found that the use of metal alkoxides in the impregnation step is advantageous because the alkoxide reagent represents an extremely pure source of the metal and metal oxide reagents, unlike water soluble salts such as the alkali metal or sulfur-containing salts which carry possibly unwanted counter-ions into the support material for incorporation into the catalyst. Upon heating or calcining, the alcohol adduct of the alkoxide is driven off or oxidized to form a metal oxide species.

Metal alkoxides are also mildly reactive toward hydroxylated supports such as porous Alundum and silica, but they are not corrosive nor overly reactive so as to harm the physical integrity of the support. This mild reactivity of the alkoxide towards the support permits tenacious binding of the metal species with the support material.

In addition to the alkoxides being easily decomposed by heating, the alkoxides are also susceptible to decomposition by direct hydrolysis, preferably in the presence of heating, such that the desired water insoluble oxides can be precipitated within the support pores by contacting the impregnated support with water and heating. This permits the treated support to be utilized for consecutive impregnations as well as post-impregnations using aqueous solutions of promoter metal ions. Also, when decomposed such as by hydrolysis, the hydrolysate is of high surface area and surface activity, conditions which often require techniques to develop which could not otherwise be applied without support destruction. A further advantage to the use of metal alkoxides in the impregnation of fluidizable supports is that metal alkoxides and mixed metal alkoxides can be co-impregnated on a given support with extremely homogeneous dispersion.

Additionally, by choosing particular alkoxy-derivatives of reducible metal ions, an in situ reduction of the metal can be effected. For example, whereas t-butoxy vanadium does not readily autoreduce, the iso- and n-butoxy species do reduce the vanadium in situ, particularly when assisted thermally. In general, we have found that alcohol adducts having alpha hydrogens cause autoreduction of reducible metals readily. Additionally, alcohol adducts having allylic hydrogens also readily initiate autoreduction.

The metal alkoxide impregnation step can be repeated to increase the amount of metal (or metal oxide) deposited within the support. After the impregnation of at least one metal alkoxide catalyst component, additional catalyst components can be added in the form of metal alkoxide solutions or solutions of other catalyst component compounds.

For the additional catalyst component compounds, the solvent may be water, alcohol, or another organic solvent including but not limited to aldehydes such as isobutyaldehyde, ketones such as methylethylketone, glycols such as ethylene glycol, carboxylic acids such as acetic acid, oxygenated aromatic compounds such as phenol or dimethylphthalate, and the like.

Supported and attrition resistant fluidizable catalysts which may be prepared by the process of the present invention include promoted and unpromoted multimetal component catalyst systems such as the vanadium phosphates, bismuth molybdates, vanadyl molybdates, antimony molybdates, phosphomolybdic acid based catalysts and the like, useful for oxidation, ammoxidation, oxydehydrogenation, hydrogenation, cyclization, dehydration reactions and the like.

Additional catalyst components, therefore, may include but are not limited to the metals contained in the above listed metal alkoxides as well as the alkali and alkaline earth metals, U, Th, Ti, Hf, Cr, W, Mn, Re, Fe, Co, Ni, the platinum group metals, Ag, Au, Cd, Tl, Sn, Pb, P, As, Bi, the rare earth metals, and mixtures thereof. The catalyst components may be introduced into solution as compounds such as oxides, hydroxides, halides, and organic and inorganic salts such as nitrates, phosphates, acetates, formates, and the like.

In one embodiment of the invention, supported and attrition resistant fluidizable vanadium and phosphorus oxide containing catalysts are prepared by the above detailed process. A vanadium alkoxide such as vanadium-t-butoxide is introduced into tert-butanol. Alternatively, the alcohol adduct of isopropanol, isobutanol, crotyl alcohol, or n-butanol and the like could be used to cause autoreduction of the vanadium. The solution of the vanadium alkoxide is contacted with the inert fluidizable support material, such as silica or Alundum, to permit impregnation. The impregnated support may be heated to drive off the alcohol adduct and effect deposition of the vanadium species, or the vanadium alkoxide may be hydrolyzed by contacting the impregnated support with water, such as by slurrying in water or by contacting with an acid, preferably inorganic. In one embodiment of the invention, the support material is wetted with water before contacting with the vanadium alkoxide, to permit the hydrolysis of the vanadium alkoxide species upon contact with the aqueous wetted pore surfaces.

In a preferred embodiment of the invention, a non-reducing alcohol adduct is utilized for the vanadium alkoxide. After the support material is impregnated with the vanadium alkoxide solution, the vanadium containing support is contacted with a solution of a phosphorus containing compound such as phosphoric acid, preferably comprising a vanadium reducing solvent such as isopropanol, isobutanol, ethylene glycol, crotyl alcohol, and the like. It is preferred that the vanadium containing support material be slurried in the phosphorus component containing solution, and heated to effect reaction of the vanadium with the phosphorus compound and additionally, the reduction of a portion of the vanadium to a +4 valence state. If a non-reducing liquid is utilized as the solvent for the phosphorus compound, the vanadium containing support may be contacted with other vanadium reducing agents, such agents being known in the art.

Preferred vanadium and phosphorus oxide catalysts for the oxidation of 4 carbon atom hydrocarbons to maleic anhydride contain vanadium in an average valence state of about 303.5 to about +4.6. This average valence state is achieved when at least a portion of the pentavalent vanadium deposited from the vanadium alkoxide solution is reduced to the +4 state. The average valence state of the vanadium is reduced preferably to about +4.1. Catalysts suitable for the production of maleic anhydride generally have a phosphorus to vanadium ratio of about 3:1 to about 0.5:1. Preferred is a P/V ratio of about 1.8:1 to about 0.9:1.

Promoter compounds such as Mo, Cu, Nb, B, Sb, Ta, Zn, and Zr can be added as alkoxides to form a promoted vanadium phosphorus oxide supported catalyst. Other promoter components, including but not limited to the alkali metals, the alkaline earth metals, Ti, Cr, W, Mn, Th, U, Co, Fe, Hf, Ni, As, Te, Bi, Sn, Ge, Cd, the lanthanides, and mixtures thereof can be introduced to the support material with the vanadium or phosphorus containing solutions, or separately in a solution or slurry of water or an organic solvent such as those listed above.

After the in situ formation of the catalyst in the pores of the support material, fluidizable supports are separated from the solution liquids, dried at a temperature above about 100° C., and may be calcined by heating the catalyst in a mixture of steam and air or air along at a temperature of about 300° C. to about 500° C. The catalyst may be calcined, if desired, either in the presence of hydrocarbon, an inert gas or both.

The attrition resistant, fluidizable impregnated catalysts prepared by the process of the present invention may be utilized in the fluid-bed reactors known in the art.

The attrition resistant vanadium and phophorus oxide containing fluidizable catalyst prepared by the process of the present invention may be utilized to form maleic anhydride from n-butane, n-butene, 1,3-butadiene or a mixture thereof. Preferred is the use of n-butane or a mixture of hydrocarbons that are produced in refinery streams. The molecular oxygen required is most conveniently added as air, but synthetic streams containing molecular oxygen are also suitable. In addition to the hydrocarbon and molecular oxygen, other gases may be added to the reactant feed. For example, steam or nitrogen could be added to the reactant. The ratio of the reactants may vary widely and are not critical. The ratio of molecular oxygen to the hydrocarbon may range from about 3 to about 30 moles of oxygen per mole of hydrocarbon. Preferred oxygen/hydrocarbon ratios are about 4 to about 20 moles of oxygen per mole of hydrocarbon.

The reaction temperature may vary widely and is dependent on the particular hydrocarbon and catalyst employed. Normally, temperatures of about 250° C. to about 600° C. are employed with temperatures of about 325° C. to 500° C. being preferred. The contact time may be as low as a fraction of a second or as high as 50 seconds. The reaction may be conducted as atmospheric, superatmospheric or subatmospheric pressure. Operation at superatmospheric pressure is preferred, from greater than 1 atmosphere to about 3 atmospheres.

SPECIFIC EMBODIMENTS OF THE INVENTION

The catalysts prepared in the examples below were tested for the production of maleic anhydride by the oxidation of butane utilizing 5 cc micro reactors comprising a 10 centimeter long glass tube of 10 mm outer diameter containing a fritted sparging disk for introduction of butane and air. Effluent gases were routed past a knockout pot to recover any expelled catalyst particles, and then routed to a gas chromatograph for analysis. Reaction conditions and results of the tests run are described in Table I. The results are stated in terms as follows:

$$\text{Single Pass Yield} = \frac{\text{Moles of Maleic Anhydride Formed}}{\text{Moles of Butane Fed}} \times 100$$

$$\text{Total Conversion} = \frac{\text{Moles of Butane Reacted}}{\text{Moles of Butane Fed}} \times 100$$

$$\text{Selectivity} = \frac{\text{Single Pass Yield}}{\text{Total Conversion}}$$

EXAMPLE 1

In order to compare the results of previously tested catalysts with the catalysts run in the 5 cc micro- unit, a fluid bed spray dried catalyst containing 80% $V_1P_{1.2}O_x$ (where x is the number of oxygens necessary to fulfill the valence requirements of the other elements) and 20% silica which demonstrated yields of maleic anhydride of greater than 50 molar percent when tested in a 1½ inch diameter laboratory fluid bed reactor, was tested in the 5 cc unit and provided yields of maleic anhydride from about 27.5 to 33.5 molar percent.

EXAMPLES 2 and 3

A catalyst of 16% by weight $V_1P_{1.2}O_x$ on alumina was prepared by heating 50 grams of Norton low surface area fluidizable alumina to between about 80° C. to about 105° C. while contacting the alumina with 50 grams of vanadyl t-butoxide (0.902 molal in vanadium) by drop wise addition. 5.76 grams of phosphoric acid was dissolved in 25 ml isobutanol, and was added to the vanadium impregnated alumina with heating from about 95° C. to about 110° C., at a rate sufficient to meet the pore volume of the alumina. Upon addition of the phosphoric acid solution, the color of the impregnated alumina changed from yellow to pale green and then to grey. The vanadium phosphorus oxide precursor-impregnated catalyst was dried at 150° C. for about 45 minutes. The dried catalyst was calcined at 400° C. for about 1 hour.

EXAMPLES 4 and 5

A catalyst of the formula 41% $V_1P_{1.2}O_x$, by weight impregnated on fluidizable silica was prepared by the following procedure. 112 grams of a vanadium alkoxide solution containing 5.26 grams of vanadium was added in six portions to 25 grams of F-7 silica (140–325 mesh or 0.044–0.105 milimeters). The vanadium alkoxide impregnated silica was dried at about 45° C. under vacuum. 12.2 grams of crystalline ortho phosphoric acid was dissolved in about 50 ml of isobutanol and the solution was added to the vanadium impregnated silica in 10 ml batches, while evaporating off the solvent at about 50° C. under vacuum. The vanadium phosphorus oxide catalyst precursor-impregnated catalyst was dried at 150° C. and later calcined.

COMPARATIVE EXAMPLE 6

A catalyst of the formula 15.3% $V_1P_{1.2}O_x$ on low surface area fluidizable alumina was prepared by dissolving a pre-formed vanadium phosphorus oxide catalyst in isobutanol by bubbling HCl through a mixture of the catalyst and isobutanol until dissolution occurred. The fluidizable alumina was contacted with portions of the catalyst-containing solution in successive increments followed by drying until the impregnation was complete. After final drying, the catalyst was calcined for 1 hour at 400° C.

COMPARATIVE EXAMPLE 7

A catalyst of the formula 40% $V_1P_{1.2}O_x$, by weight on F-7 silica was prepared by impregnating 4 grams of the silica in two steps with 23 grams of a catalyst containing solution prepared as in Example 6. The impregnated catalyst was dried and calcined at 400° C. for 1 hour.

COMPARATIVE EXAMPLE 8

Vanadium pentoxide was melt deposited on F-7 silica and contacted with a solution of ortho phosphoric acid in isobutanol with heating to form a catalyst of the formula 40% $V_1P_{1.2}O_x$ on silica, the vanadium having been reduced by cntact with ammonia.

TABLE I

Oxidation of N—Butane to Produce Maleic Anhydride Using Attrition Resistant Fluidizable Supported Catalysts Containing the Mixed Oxides of Vanadium and Phosphorus.

| Example No. | Temperature (°C.) | Contact Time (Sec.) | % Conversion | Maleic Anhydride % Yield | % Selectivity |
|---|---|---|---|---|---|
| 2 | 400 | 2 | 53.2 | 28.1 | 52.8 |
| 3 | 421 | 2 | 56.1 | 30.6 | 54.6 |
| 4 | 400 | 2 | 69.0 | 30.2 | 43.8 |
| 5 | 400 | 2.1 | 66.6 | 22.8 | 34.2 |
| C6 | 400 | 2 | 36.2 | 12.0 | 33.1 |
| C7 | 401 | 2 | 45.0 | 16.1 | 35.8 |
| C8 | 400 | 2 | 25.1 | 8.9 | 35.4 |

As is demonstrated in Table I, catalysts supported on carriers which exhibit a high attrition resistance can be prepared by impregnation of the carrier with a metal alkoxide with subsequent treatment to include additional catalyst components to render highly active catalysts comparable in activity to less attrition resistant forms prepared by conventional methods. Also, the preparation of the catalyst by the impregnation of the metal alkoxide species results in an impregnated or supported catalyst having higher activity than impregnated or supported catalysts prepared by conventional techniques.

Although specific embodiments of fluidizable catalysts have been exemplified by the impregnation of fluidizable supports with the metal alkoxide component to provide highly attrition resistant fluid-bed catalysts, the process of the present invention is equally suitable to the metal alkoxide impregnation of supported catalysts of the type conventionally utilized in fixed-bed reactor systems. Generally, attrition resistance is not as critical in fixed-bed operations, and hence the process of the present invention is most particularly suited for the preparation of fluid-bed catalysts. Highly active fixed-bed catalysts can be prepared by the above method, however, by substituting fixed-bed forms of the desired support material for the fluidizable support. The resulting impregnated catalysts may then be loaded and utilized in conventional fixed-bed reactors.

Thus it should be apparent to those skilled in the art that the subject invention accomplishes the objects set forth above. It is to be understood that the subject invention is not to be limited by the examples set forth herein. These have been provided merely to demonstrate operability and the selection of metal alkoxides, additional catalyst component compounds, liquid media, catalyst support or carriers, feed stocks and reaction conditions can be determined from the total specification disclosure provided without departing from the spirit of the invention herein disclosed and described, the scope of the invention including equivalent embodiments, modifications and variations that fall within the scope of the attached claims.

We claim:

1. A process for the production of maleic anhydride by the oxidation of 4 carbon atom hydrocarbons with molecular oxygen or an oxygen containing gas in the vapor phase at a reaction temperature of about 250° C. to about 600° C. in the presence of a catalyst containing the mixed oxides of vanadium and phosphorus wherein said catalyst is prepared by impregnating a preformed catalyst support with a first solution of a vanadyl alkoxide, contacting the impregnated support with a second solution of the phosphorus component to form the catalyst in situ, drying the catalyst containing support.

2. A process as in claim 1 wherein said support is fluidizable.

3. A process as in claim 1 wherein said first or second solution contains at least one additional catalyst component selected from the alkali metals, Ti, Cr, W, Mn, Th, U, Co, Fe, Hf, Ni, As, Te, Bi, Sn, Ge, Cd, the lanthanides, Mo, Cu, B, Sb, Ta, Nb, Zn, Zr and mixtures thereof.

4. A process as in claim 1 wherein said catalyst support is additionally impregnated with an alkoxide of at least one metal selected from Mo, Cu, B, Sb, Ta, Nb, Zn, Zr and mixtures thereof.

5. A process as in claim 1 wherein said first or second solution comprises an organic liquid capable of effecting reduction of a portion of the vanadium to a +4 valence state.

6. A process as in claim 1 wherein said alkoxide is capable of autoreducing the vanadium.

* * * * *